United States Patent
Huang (10) Patent No.: US 8,236,165 B2
(45) Date of Patent: Aug. 7, 2012

(54) METHOD FOR OPERATING MEASURING METER AND MEASURING METER

(75) Inventor: Chun-Mu Huang, Dali (TW)

(73) Assignee: Bionime Corporation, Dali, Taichung County (TW)

( * ) Notice: Subject to any disclaimer, the term of this patent is extended or adjusted under 35 U.S.C. 154(b) by 1002 days.

(21) Appl. No.: 11/799,855

(22) Filed: May 2, 2007

(65) Prior Publication Data

US 2007/0272564 A1 Nov. 29, 2007

(30) Foreign Application Priority Data

May 24, 2006 (EP) ................................. 06114494

(51) Int. Cl.
*G01N 27/26* (2006.01)
*G01N 27/327* (2006.01)

(52) U.S. Cl. .............. 205/792; 205/778; 205/777.5; 204/403.11; 204/403.04; 422/82.01; 600/347

(58) Field of Classification Search .......... 204/403.01–403.15; 205/775, 205/792, 777.5, 778; 600/345–348; 422/82.01, 422/82.02

See application file for complete search history.

(56) References Cited

U.S. PATENT DOCUMENTS

| 4,897,162 | A | * | 1/1990 | Lewandowski et al. ...... 205/786 |
| 5,108,564 | A | | 4/1992 | Szuminsky et al. |
| 5,260,663 | A | * | 11/1993 | Blades ............................ 324/442 |
| 5,266,179 | A | | 11/1993 | Nankai et al. |
| 5,366,609 | A | * | 11/1994 | White et al. .............. 204/403.04 |
| 5,620,579 | A | * | 4/1997 | Genshaw et al. ............. 204/402 |
| 5,766,934 | A | * | 6/1998 | Guiseppi-Elie ............ 435/287.9 |
| 6,827,829 | B2 | * | 12/2004 | Kawanaka et al. ........ 204/403.02 |
| 2005/0045476 | A1 | * | 3/2005 | Neel et al. .................. 204/403.02 |
| 2006/0231425 | A1 | * | 10/2006 | Harding et al. ................ 205/792 |

FOREIGN PATENT DOCUMENTS

| EP | 1 272 833 B1 | 11/2004 |
| WO | WO98/58250 | * 12/1998 |
| WO | WO01/21827 | * 3/2001 |

* cited by examiner

*Primary Examiner* — Jeffrey T Barton
*Assistant Examiner* — Jennifer Dieterle
(74) *Attorney, Agent, or Firm* — Volpe and Koenig, P.C.

(57) ABSTRACT

A method for operating a measuring meter for an electrochemical test strip is provided. The method comprises steps of applying a voltage to electrodes of the test strip at least during one of a sample presence detection period and an incubation period; and repeatedly increasing and decreasing the voltage during at least one of the sample presence detection period and the incubation period.

21 Claims, 10 Drawing Sheets

METHOD FOR OPERATING MEASURING METER AND MEASURING METER

FIELD OF THE INVENTION

The present invention relates to a method for operating a measuring meter and to a measuring meter, and more particularly to a method for operating a measuring meter for an electrochemical test strip.

BACKGROUND OF THE INVENTION

Electrical sensor systems for analyzing analytes in biological samples are widely used. For example, analytes such as glucose level, cholesterol level or uric in a sample such as blood may be analysed. In general, such electrochemical measuring systems include a test strip and a measuring meter. In particular, test strips are provided as single use, disposable strips for easy home use.

In particular, electrochemical sensors using enzymatic amperometric methods are well known. The sensors of such systems have electrodes coated with a reagent including enzymes. The electrodes are used to sense an electrochemical current produced by a reaction between the reagent and the analyte or the analytes in a test sample. The enzyme is used for a unique, well specified reaction with a specific analyte in the test sample. This specific reaction reduces the interference with other analytes. A reagent with a specific cholesterol enzyme may e.g. be used to test the cholesterol level in a sample. A reagent with a glucose oxidase enzyme may be used to measure the glucose level in a blood sample. The glucose oxidase does not react with cholesterol. Neither does it react with other sugars in the blood sample. The use of glucose oxidase e.g. typically leads to a 99% unique selection of glucose within the sample. Methods based on the use of enzyme are leading to most accurate measurement results.

Currently, a plurality of generations of amperometric methods have been developed for analysis of the glucose level in a blood sample.

In a first generation of glucose analysis, the reagent covering the sensor includes glucose oxidase enzymes (hereinafter referred to as GOD). The mechanism of the reaction between the glucose in the sample and the enzyme and subsequent detection are as follows:

$$\text{Glucose} + \text{GOD}_{(ox)} \rightarrow \text{Gluconic acid} + \text{GOD}_{(red)} \tag{1}$$

$$O_2 + \text{GOD}_{(red)} \rightarrow H_2O_2 + \text{GOD}_{(OX)} \tag{2}$$

$$H_2O_{2(Apply\ Voltage)} \rightarrow O_2 + 2H^+ + 2e^- \tag{3}$$

GOD has two forms. In equation (1), GOD is present in its natural, oxidised form $\text{GOD}_{(ox)}$ before its reaction with glucose. In the reaction with glucose, GOD is changed to the reduced form $\text{GOD}_{(red)}$.

After reaction with oxygen $O_2$, $\text{GOD}_{(ox)}$ is returned to the oxidised form $\text{GOD}_{(ox)}$ (see equation (2)). In this reaction, hydrogen peroxide $H_2O_2$ is created. GOD is oxidised again, will be still present in the reagent and can be reused for a reaction according to equation (1). The amount of produced $H_2O_2$ is proportional to the level of glucose in the sample, provided there is a sufficient amount of oxygen $O_2$ present. If the amount of $H_2O_2$ can be determined, the glucose level can be determined. In order to measure the amount of $H_2O_2$ produced, a predetermined voltage is applied to the electrodes such as to oxidise $H_2O_2$ (see equation (3)). By oxidation, two electrons $e^-$ will be delivered and $H_2O_2$ will be oxidised to oxygen $O_2$ and two hydrogen $2H^+$. Oxygen $O_2$ again can be used in the reaction according to equation (2). The electrons generated at the electrodes provide a current. This sensing current is proportional to the glucose level in the sample.

This first generation glucose analysis method has some drawbacks which are in particular due to an insufficient amount of oxygen $O_2$ initially present before the start of the reaction process. Especially in home use applications based on disposable test strips of glucose sensors, reagents of a dry type are used in view of long storage time. In such sensors, initial oxygen is provided by the blood sample only. While there is some oxygen inside a fresh blood sample, this may be an insufficient amount especially for high concentrations of glucose. This may lead to measurement errors. Furthermore, red blood cells within the sample may continuously consume oxygen so that oxygen will be exhausted. An insufficient amount of oxygen may lead to a reading error. This phenomenon is known as the oxygen dependence problem.

In order to solve the oxygen dependence problem, in a second generation of glucose sensor, electron carrying mediators are used in the reagent. Typically, potassium ferrocyanide is used as a mediator. In case of strips using such mediators, the reaction is as follows:

$$\text{Glucose} + \text{GOD}_{(ox)} \rightarrow \text{Gluconic acid} + \text{GOD}_{(red)} \tag{4}$$

$$\text{GOD}_{(red)} + 2M_{(ox)} \rightarrow 2M_{(red)} + \text{GOD}_{(OX)} + 2H^+ \tag{5}$$

$$2M_{(red)(Apply\ Voltage)} \rightarrow 2M_{(ox)} + 2e^- \tag{6}$$

In the above equations, $M_{(ox)}$ represents the oxidised and $M_{(red)}$ represents the reduced form of the mediator. The reaction as shown in equations (4) to (6) are such that during a reaction cycle a sensing current is produced which depends on the concentration of the glucose in the blood sample. The whole reaction process is thus basically independent of the amount of oxygen in the sample. However, the effect from oxygen during the mediator reaction cannot be fully avoided. Equation (4) is basically identical to equation (1) shown above. Oxygen $O_2$ present in the initial blood will react with the reduced form of GOD and thereby also create hydrogen peroxide $H_2O_2$ as shown in equation (2). If a predetermined voltage is applied to the electrodes in order to oxidise the mediator in reaction (6), the same voltage will lead to oxidation of $H_2O_2$. Electrons based on oxidation of $H_2O_2$ (as shown in equation (3)) will thus be generated at the electrodes. In consequence, the sensing current is constituted by two parts. A first part is based on oxidation of the mediator in the reduced form (see equation (6)). A second part of the current is based on the reaction (3) shown above. Because of the unstable amount of oxygen in the blood sample, this secondary current is unstable. The measurement result is thus unstable. This phenomenon is also called the oxygen interference.

There have been several proposals in order to overcome the oxygen interference in the second generation of glucose sensors. One solution is to replace the glucose oxidase enzyme with glucose dehydrogenase (GDH). Because GDH does not react with oxygen such as to create $H_2O_2$, there is no oxygen interference. However, there are some drawbacks with respect to the use of GDH. In particular, the selectivity with respect to glucose is only about 80 to 90%. The GDH does not only react with glucose but also with other sugars present in the blood such as maltose. While the use of GDH reduces the oxygen interference problem, it creates another interference problem, leading to erroneous readings of the glucose level.

In order to determine the concentration of the analyte in the sample, the sensing current is measured. The sensing current is called the Cottrell current, according to the following equation:

$$i(t) = K \cdot n \cdot F \cdot A \cdot C \cdot D^{0.5} \cdot t^{-0.5}$$

Where: i is an instant value of the sensing current;
K is a constant;
n is the transferred number of electrons (For example, n is 2 in the equation (6));
F is the Faraday constant;
A is the surface area of the working electrode;
C is the concentration of the analyte in the sample;
D is the diffusion coefficient of the reagent;
t is a specified time after a predefined voltage has been applied to the electrodes.

The concentration C of the analyte shall be determined. This concentration is proportional to the sensing current i. Because the sensing current is also proportional to the surface area A of the working electrode, a precisely defined surface area of the working electrode of the test strip is a key factor in view of an accurate measurement.

Furthermore, as shown in the Cottrell Equation, the time dependent value of the sensing current decreases with the square root of the duration after the time when the predefined voltage has been applied to the electrodes. The control of the point in time when a voltage is applied to the electrodes and when the Cottrell current is determined is a further important factor in view of accurate measurements.

Examples of such sensors and test meters are e.g. disclosed in U.S. Pat. No. 5,266,179, U.S. Pat. No. 5,366,609 or in EP 1 272 833.

The operation principle of the measuring meters disclosed in these documents is generally the same. First, a test strip is inserted into the measuring meter. A proper insertion of the test strip within the meter is detected by mechanical and/or electrical switches or contacts. Once a test strip is properly inserted into the measuring meter, the user is asked to provide a sample, typically a drop of blood. The sample of blood is then fed to a reaction zone on the test strip. The reaction zone of the test strip is provided with at least two electrodes which are covered by the reagent.

In order to detect presence of a sample in the reaction zone, secondly, a voltage is applied to the electrodes. The resistance of the reagent between the electrodes without the presence of a sample is high. As soon as a sample is present in the reaction region, the resistance between the electrodes is reduced. Reduction of the resistance leads to flow of a current which may be detected as an indication of the presence of a sample.

A further drawback of known measuring meters is related to such detection of sample presence. In a sample detection period, a voltage is applied to the electrodes for verifying whether or not a sample is present. This voltage, however, leads to consumption of the current (i.e. consumption of electrodes) which is produced as a result of the reaction between the reagent and the testing sample. The current is related to the concentration of the analyte in the sample. The consumption of current during sample pressure detection leads to measurement errors. This problem is particularly relevant if the sample of the analyte is relatively small or if the detection time in the measurement system is relatively short. Especially for home use measuring systems, the volume of the sample and the detecting time of the measuring meters has been recently reduced in order to increase the usability and the user friendliness of such test strips. Typically, the volume of blood samples has been reduced from originally 10 mL to actually around 0.3 mL. The total detecting time has been reduced from originally about 60 seconds to actually about 5 seconds.

Once a sufficient amount of sample is present in the reaction zone, in a second step mixing of the sample with the reagent is allowed for a certain period of time. This period of time is also called incubation time. After completion of incubation, in a third step, the measurement starts.

Another problem of known devices is related to the incubation time. Incubation time is used in order to allow mixing and melting of the sample with the reagent. A certain time is needed for completion of this mixing and melting. The completion of the melting is affected by parameters such as the ambient temperature or sample blood conditions of the user. The melting is e.g. slow at low ambient temperature or with patients having a high fat proportion within the blood. If measurements are made before melting has been completed, an unstable measuring current will result. Consequently, currently, a sufficient incubation time must be selected such as to be suitable for the longest melting conditions in order to guarantee a precise and accurate measurement under all circumstances.

If a voltage is applied during incubation, current starts to be consumed during the incubation period. Because of different melting conditions, the amount of consumption is unstable. Therefore, again, measurement errors would be caused if a voltage is applied.

Operation and drawbacks of such prior art meters will be explained in more detail in FIGS. 3A to 3C.

Some prior art documents such as U.S. Pat. No. 5,108,564 suggest to make incubation in an open circuit. This measurement principle has, however, also certain drawbacks. During the incubation time, small oxygen bubbles are created in the sample if no voltage is applied. Generation of oxygen bubbles is due to the following process. As mentioned above, the use of electron mediators solves the oxygen dependency problem in context with first generation strips. However, as mentioned above, there is still a problem of oxygen interference. One solution to the oxygen interference problem is to select a specific mediator material only requiring a low voltage such as to oxidise the mediator as shown in equation (6). If the voltage necessary to oxidise the mediator is insufficient to oxidise $H_2O_2$ as shown in equation (3), the oxygen interference can be reduced to an extent at which it can be ignored. In particular, the ratio between primary and secondary current can be increased to 20 to 1 or even above 150 to 1 when the predefined voltage is applied to the electrodes during the measurement time period.

No voltage is applied during the incubation time according to the conventional measuring meters. If no voltage is applied, the reaction processes of the equations (3) and (6) will be stopped during incubation time. At the beginning of incubation time, glucose will react with the oxidised form of the glucose oxidase $GOD_{(ox)}$, thereby reducing GOD to the reduced form $GOD_{(RED)}$. Because the reduced form of the mediator cannot be oxidised into its oxidised form $M_{(ox)}$ without application of the predefined voltage to the electrodes, $GOD_{(RED)}$ will react with both the mediator and oxygen in accordance with equations (2) and (5). The reaction according to equation (5) will be stopped once the mediator present in the reagent has been brought to the reduced form $M_{(RED)}$.

In parallel, initial oxygen within the fresh blood will create $H_2O_2$ in accordance with equation (2). $H_2O_2$ cannot be oxidised to $O_2$ and $2H^+$ and electrons in accordance with equation (3) if no voltage is applied to the electrodes. However, $H_2O_2$ will naturally dissolve into oxygen $O_2$ and water $H_2O$ under the effect of temperature, as shown in equation (7). Furthermore, if no voltage is applied, a metal electrode catalyzes the dissolution of $H_2O_2$ to $O_2$ and $H_2O$ in accordance with the following equation (8):

$$H_2O_{2(under\ temperature)} \rightarrow O_{2(gas)\uparrow} + H_2O \qquad (7)$$

$$H_2O_{2(catalysis\ by\ metal)} \rightarrow O_{2(gas)\uparrow} + H_2O \qquad (8)$$

Initially, oxygen $O_2$ is uniformly distributed within the fresh sample. Because the reaction in accordance with equation (8) above is catalysed by the metal electrodes, $O_2$ will accumulate in the form of small bubbles in the area of the electrode surface. Because usually a capillary channel will be formed neighbouring the electrodes in order to automatically suck the sample into the reaction zone, oxygen bubbles attached to the electrode can-not easily disappear. Consequently, the effective working area of the electrode is reduced by accumulation of oxygen bubbles. As a consequence, the measuring current after incubation time will be affected. Especially if small sample volumes are used, the effect of oxygen bubbles attached to the electrode surface may become relatively important such that measurement errors may become considerable. In particular, if electrodes made of a noble metal are used, formation of such oxygen bubbles may become important.

In EP 1 272 833, it has been suggested to apply a voltage during incubation time or during sample detection time which is, however, relatively low. This solution does not solve the problem of creation of oxygen bubbles.

It is therefore an object of the present invention to overcome the drawbacks of the prior art, in particular to provide a method for operating a measuring meter which allows for very accurate analyte measurements even if the volume of sample used is relatively small and/or the measuring time is short.

It is in particular an object of the present invention to provide a solution to the competition between the reaction involving oxygen in accordance with equation (2) and a reaction involving a mediator in accordance with equation (5) in second generation test strips, i.e. to reduce the oxygen interference. It is a further object of the present invention to increase the accuracy of measurements by maintaining a stable and precise surface area of the working electrode. It is a further object of the invention to provide a measurement strip and a meter which allow for a precise timing of incubation time and measurements.

According to the present invention, these and other objects are solved with a method for operating a measuring meter and with a measuring meter according to the features of the characterising portion of the independent patent claims.

SUMMARY OF THE INVENTION

The invention relates to a method for operating a measuring meter which is used with electrochemical test strips. For preparation of the measurement, i.e. before measurement of a current related to the analyte concentration is started, a voltage is applied to the electrodes of the test strip at least during one of a sample presence detection period and a incubation period. According to the present invention, the voltage applied is repeatedly increased and decreased at least during one of the sample presence detection period and the incubation period, i.e. switched repeatedly between predetermined first and second values. A repeatedly increasing and decreasing voltage in context with the present invention means, that in certain periods of time, the applied voltage is lower than during other periods in time. The applied voltage is thus changing at least once, preferably a plurality of times during sample presence detection and/or incubation. This repeated increase and decrease, i.e. repeated change of voltages during sample presence detection and/or incubation typically may consist of a pulsed voltage, i.e. a voltage continuously switching between a zero or low and a higher, maximum amplitude. However, other forms of varying potentials are conceivable.

Minimum and maximum values may be constant during one of said period or in both periods. The voltage applied may also be repeatedly increased and decreased whereby minimum and maximum amplitudes are not constant.

By application of a repeatedly varying voltage, the drawbacks of the prior art may be avoided. During sample presence detection, presence of a sample will be detected, as soon as a current flows when the voltage is relatively high, i.e. sufficiently high for detection. On the other hand, because of a relatively low voltage between subsequent maximum values of the voltage, the overall consumption of electrons during sample presence detection is reduced.

Similarly, during incubation, the repeated or regular application of a voltage inhibits creation of oxygen bubbles in the sample. Moreover, the overall consumption of electrons during incubation time is reduced because there is no constant, relatively high voltage which is applied to the electrodes.

While repeatedly varying pulses only during incubation period or only during sample presence detection have certain advantages, it is especially preferred to apply repeatedly varying pulses during both sample presence detection and incubation periods. In this case, repeatedly varying pulses may be the same (having same amplitudes, duty cycle) or may differ from each other during each of these periods.

Of course, it is also possible to apply a constant high voltage during one of the incubation period and the sample detection presence period while applying a repeatedly varying voltage during the other of these periods.

According to a preferred embodiment, the voltage is applied in a regular pattern with a predetermined or predeterminable frequency whereby the first and second voltage values correspond to a maximum and minimum values which are substantially constant at least during each of the periods. Application of a regular pattern with predetermined frequency and amplitudes is particularly easily feasible with standard controllers.

In particular, according to the present invention, the voltage during sample detection period and/or during the incubation period may be applied as a series of pulses.

According to a first embodiment of the invention, the minimum value, i.e. the value of the voltage between two pulses may be 0 Volt. In an alternative embodiment, the minimum value may be above 0 Volt, but still relatively small in order to avoid consumption of electrons.

The maximum value of the predefined voltage, i.e. the amplitude of the pulses during incubation period, is selected such as to be sufficiently high to oxidise the reduce form of a mediator $M_{(red)}$ in a reagent of a test strip to its oxidised form $M_{(ox)}$, but preferably sufficiently low so as to avoid oxidation of $H_2O_2$ in the reagent.

The maximum value for the voltage during the sample presence detection period is selected such as to be sufficient for sample detection. Depending on measurement arrangements used, this maximum value may be relatively low, in particular lower than the maximum value of the voltage during incubation time.

Typically, during the sample presence detection period, the duration of a pulse may be between 10 μs and 300 μs, and time delay between successive pulses may be between 10 ms and 50 ms. In particular, a duration of a pulse of 100 μs and a time difference between successive pulses of 20 ms was found to be appropriate.

The duration of the pulses and the time delay between successive pulses in the incubation period is selected in such a way as to have a sufficient reaction according to equation (6) such as to allow for the oxidised form mediator regeneration in order to prevent or reduce production of oxygen bubbles. The duration of the pulses is, however, selected as small as possible in view of maximum reduction of electron consumption. Typically, the duration of a pulse may be between 10 μs and 1 ms, and time delay between successive pulses may be between 10 ms and 300 ms. In particular, a duration of a pulse of 100 μs and a time difference between successive pulses of 200 ms was found to be appropriate for conventional reagents. It is, however, possible to vary duty cycles, pulse durations and frequency depending on specific applications or measurement conditions.

The measuring meter according to the present invention is used for reading values of a current flowing between electrodes of an electrochemical test strip when an analyte is present in a reaction zone of the strip. The meter has means for application of a voltage to the electrodes of the test strip. These means are designed to apply a voltage which is repeatedly changed, i.e. increased and decreased. Such a repeatedly varying voltage is applied at least during one of a sample presence detection period and an incubation period.

According to another aspect of the invention, the measuring meter is provided with a current measuring unit designed in such a way that the current flowing during incubation time is limited by saturation of electronic components in the unit, in particular by the saturation voltage of an operation amplifier of a current to voltage converter. The measuring meter comprises means for limiting current flow during incubation time, in particular through saturation. According to still another aspect of the invention, there is provided a measuring method where during incubation time current flow is limited, in particular by saturation. While such an embodiment is particularly useful in context with the repeatedly varying pulses during incubation in accordance with the present invention, it is basically also conceivable to use such a meter and method in context with other measuring meters or measuring methods.

The invention will now be shown and explained in more detail on behalf of the following embodiments and the accompanying drawings, in which:

DETAILED DESCRIPTION OF THE PREFERRED EMBODIMENT

Figure 1:
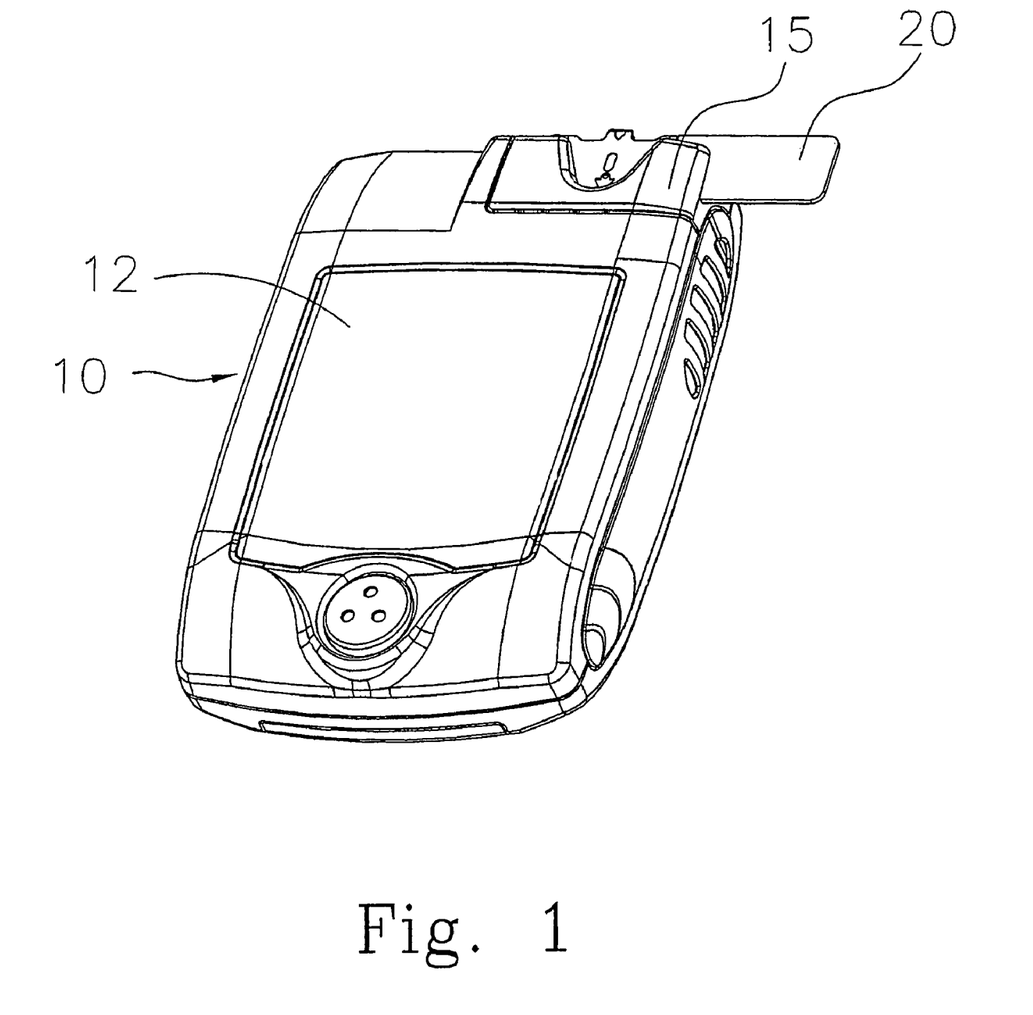
FIG. 1 is a perspective view of a measuring meter with a electrochemical test strip.

FIG. 1 shows a perspective view of a measuring meter 10 according to the present invention. The measuring meter 10 comprises a housing with a display 12 for display of measurement values. The measuring meter 10 includes a slot 15 for insertion of an electrochemical test strip 20. The test strip 20 is shown in more detail in FIGS. 2A to 2D.

Figure 2A:
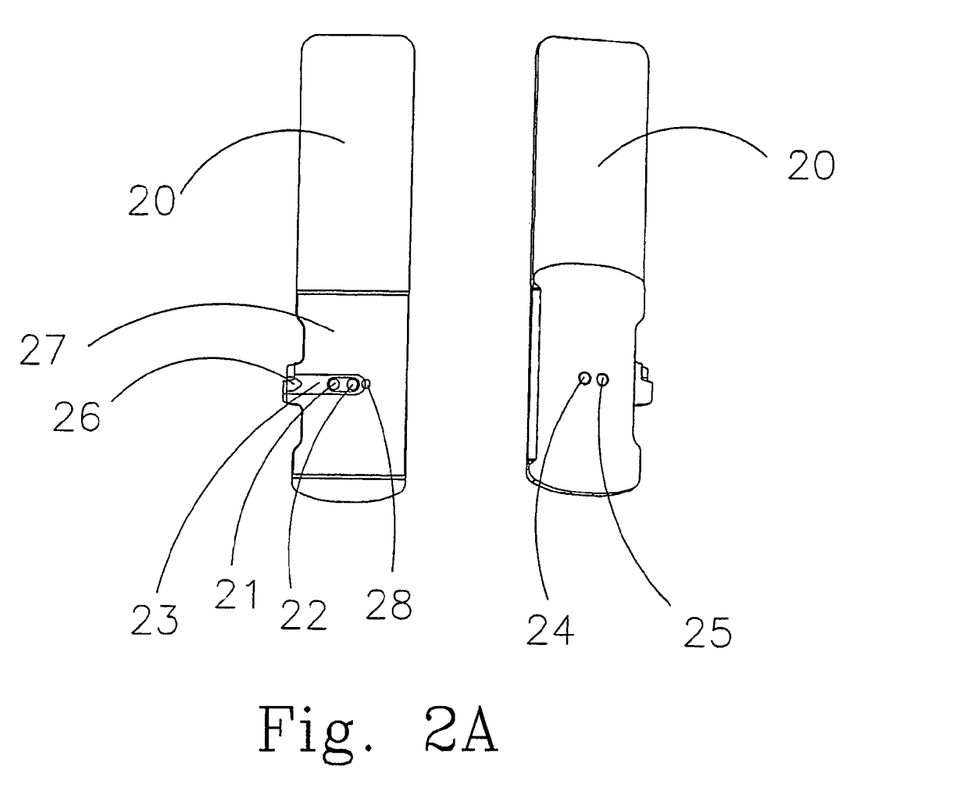
FIG. 2A is a top and bottom view of an electrochemical test strip.
Figure 2B:
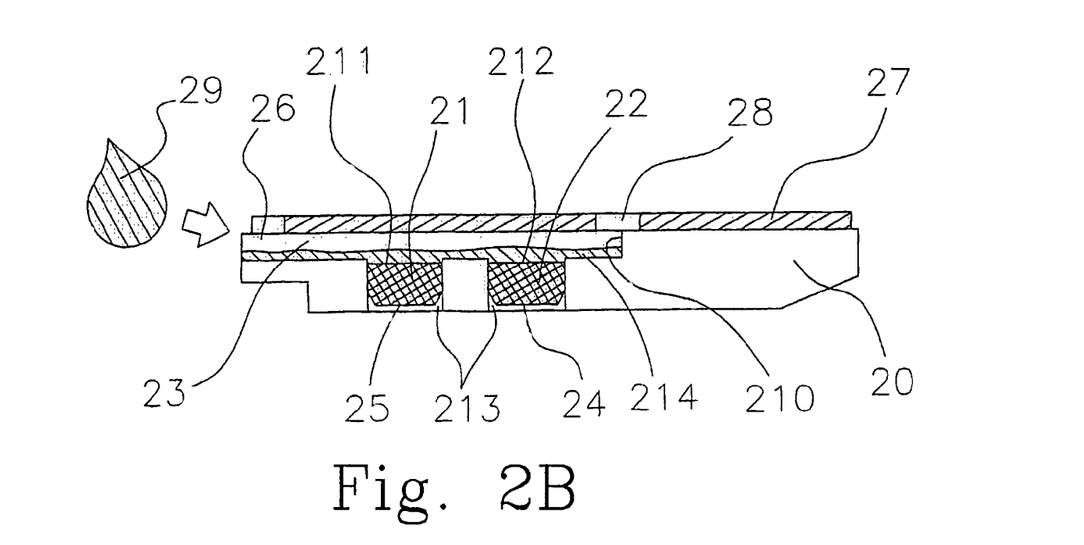
FIG. 2B is a section through the test strip according to FIG. 2A.

Left part of FIG. 2A shows a top view and the right part of FIG. 2A shows a bottom view of the test strip 20. FIG. 2B shows a cross section through the test strip shown in FIGS. 2A and 2B.

Electrodes 21, 22 are mounted in through holes 213 arranged in a recess 210 of the test strip 20. The peripheral areas of the electrodes 21, 22 are tightly surrounded by the through holes 213 without a gap being formed. The diameter of the through holes 213 is formed slightly smaller than the diameter of the electrodes such that the electrodes are mechanically held in the through holes 213.

The upper surfaces 211, 212 of the electrodes 21, 22 form a working area of the electrode. The lower side 24, 25 of the electrode form output contacts of the test strip. These output contacts may be brought into electrical connection with respective contacts 413, 414 of the sensing meter 10 (see FIG. 4).

A hydrophilic cover 27 with an air hole 28 is arranged such as to cover the recess 210 and such as to form a capillary channel 23. The capillary channel 23 defines a reaction zone. In the reaction zone, there is provided a reagent 214 coated in the recess 210 and covering the upper surfaces 211, 212 of the electrodes 21, 22. The reagent comprises in a known manner an enzyme such as a glucose oxidase, a mediator such as a potassium ferrocyanide and some hydrophilic chemical elements. The composition of the reagent is known in the art and is not part of the present invention. The sensor strip is furthermore provided with a sample inlet 26 for placing a droplet of a liquid sample 29, e.g. a droplet of blood.

Figure 2C:
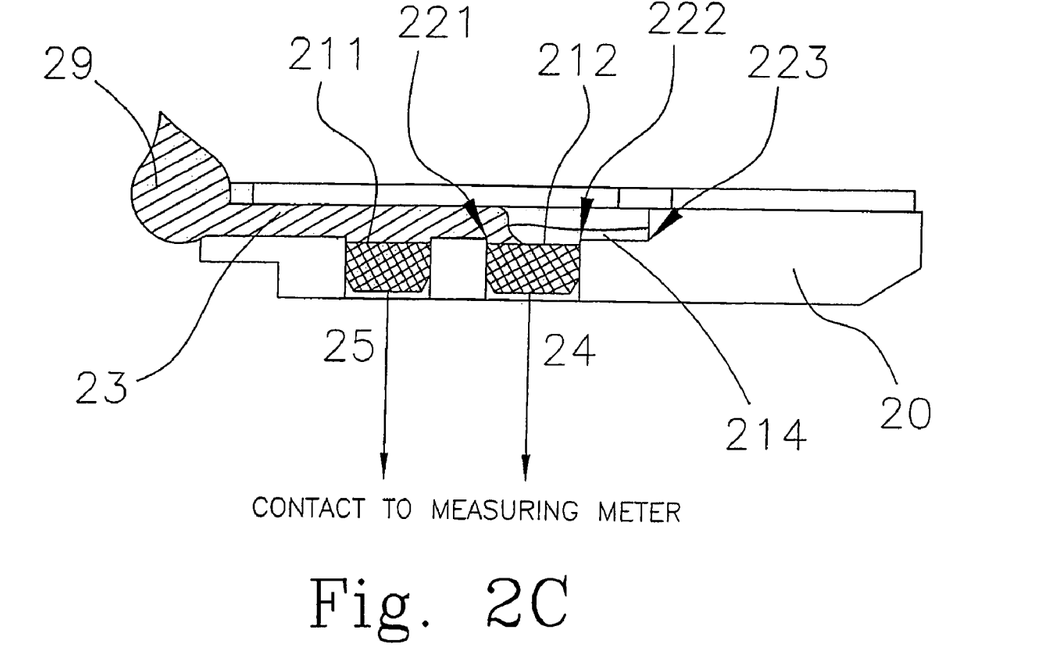
FIGS. 2C-2D are schematic views of a test sample flowing into the test strip shown in FIG. 2B.
Figure 2D:
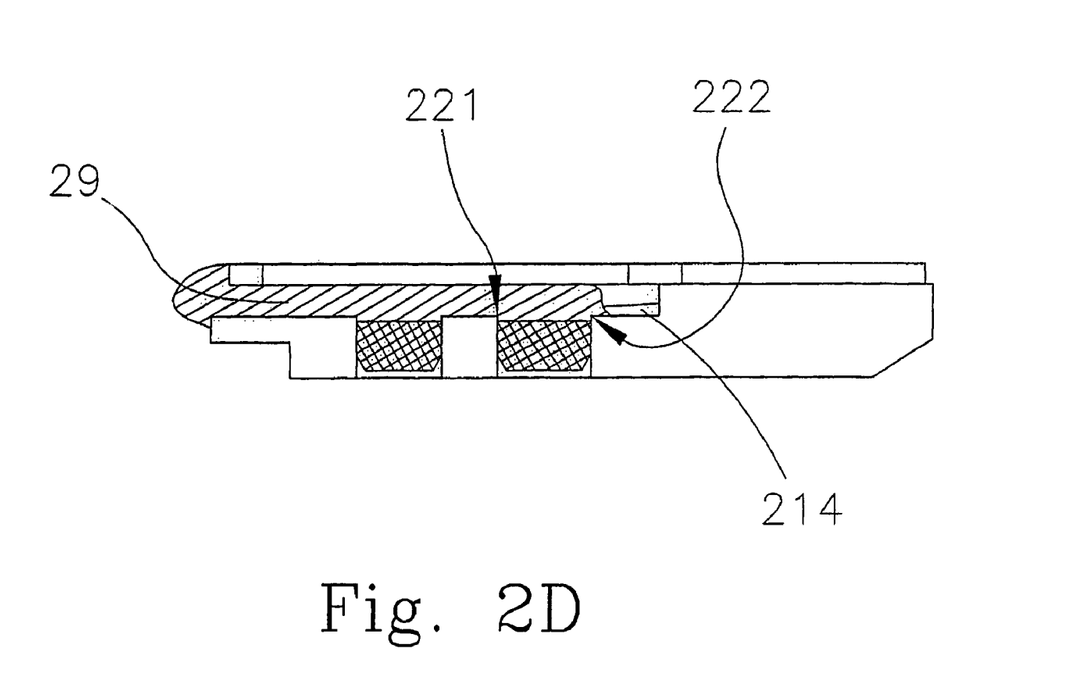

When a blood sample 29 is placed onto an opening of the sample inlet 26 (see FIG. 2C), the droplet is automatically sucked into the capillary channel 23 by capillary action or hydrophilic action. FIGS. 2C and 2D show the flow of a droplet of blood sample 29. When the sample is applied to the inlet 26 of the test strip, it begins to flow through the capillary channel 23 (see FIG. 2C) until it completely covers the electrodes (see FIG. 2D). Air contained in the capillary channel may exit through the opening 28.

In order to more clearly explain the differences of the method in accordance with the present invention as compared to the conventional methods, the conventional methods will now be explained with reference to FIGS. 3A to 3C.

Figure 3A:
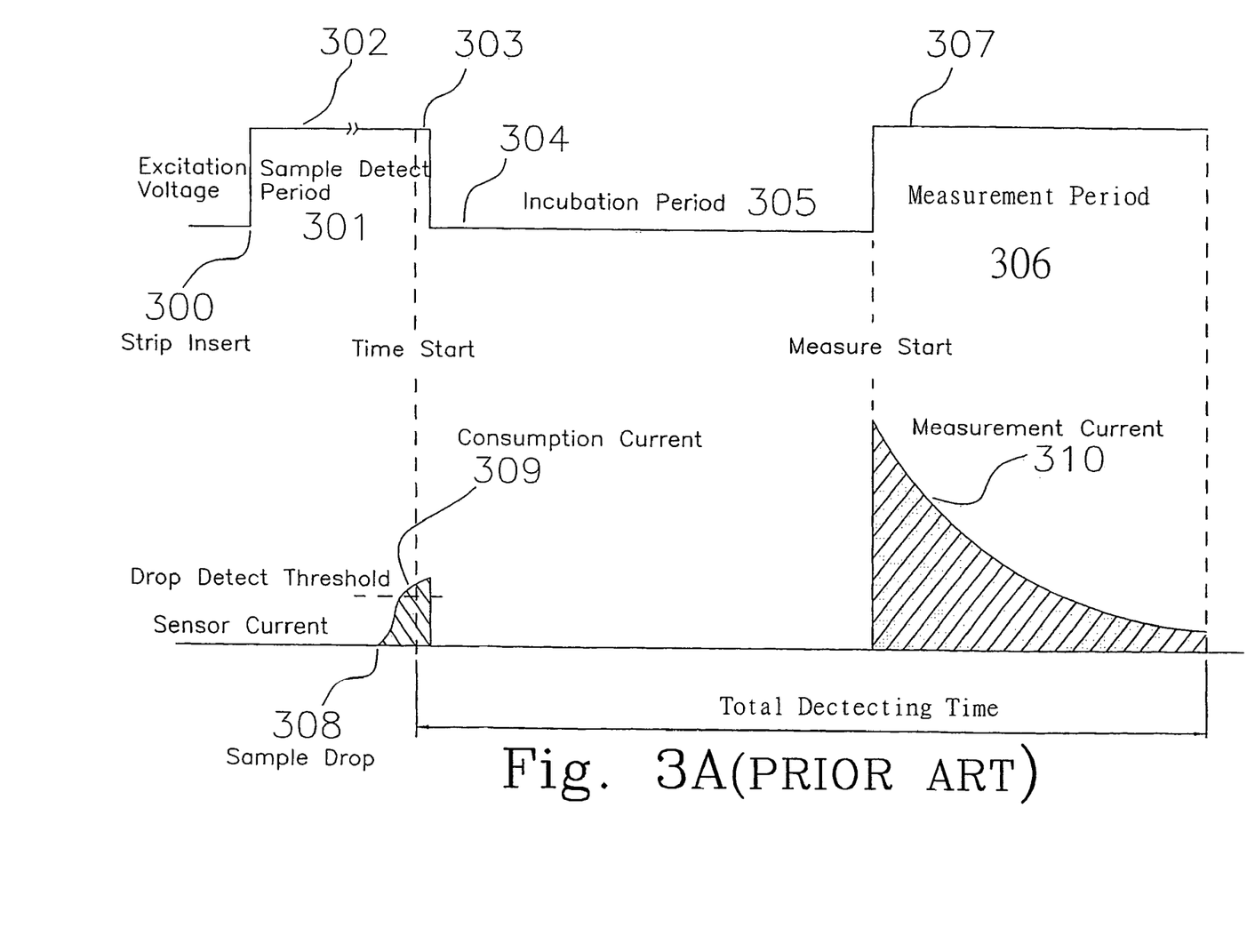
FIG. 3A is a schematic representation of voltages applied to a measuring meter according to the conventional methods.

FIG. 3A shows a method carried out by a measuring meter in accordance with the prior art, e.g. in accordance with the disclosure of U.S. Pat. No. 5,366,609. FIGS. 3B to 3C show enlarged views of the consumption current created during sample detection because of application of a voltage.

In accordance with FIG. 3A, a fixed voltage 302 is applied to the electrodes once the sensor strip has been inserted at the time 300 into the measuring meter such as to detect the presence of a test sample during a detection period 301 in the reaction zone. A drop of a sample is applied to the sensor strip at the time 308. FIG. 3B shows in enlarged form the current flowing between the electrodes when presence of a sample drop will be detected.

A sample size delay time 314 is applied once a presence of a drop has been detected at the time 316 when the flowing current has reached a drop detection threshold 312. In order to continuously verify whether the sample size has become sufficient, the measuring meter thus continuously applies the fixed voltage 302 to the electrodes until a point in time 303 (see FIG. 3A) after the time 316 when presence of the sample has been detected.

Thereafter, the amplitude of the flowing current 309 is compared with a sample size threshold 313 at the moment 315 defining the end of the sample size delay time 314. If the amplitude is below the sample size threshold 313, the measuring meter will generate an alarm indicating that insufficient sample is present in the sensor strip. The measuring process will then be stopped.

If a sufficient amount of sample is found to be present in the reaction zone, i.e. if the amplitude of the current is above the sample size threshold 313 at the moment 315, the measuring meter continues to the next process step, i.e. to the start of incubation period 305. During the incubation period 305, the measuring meter turns off the fixed voltage 302 to a zero value 304. During this incubation period 305, mixing and melting of the sample with the reagent is allowed for a certain, predetermined period of time. After completion of the incubation, the meter starts a measurement period. For this purpose, a predetermined voltage 307 is applied to the electrodes. The current 310 (see FIG. 3A, lower part) flowing between the electrodes is measured.

Determination of the concentration of analytes is made on the basis of this so called Cottrell Current. The concentration value determined on the basis of the Cottrell Current during a measurement period 306 will be displayed on a display of the meter.

Figure 3B:
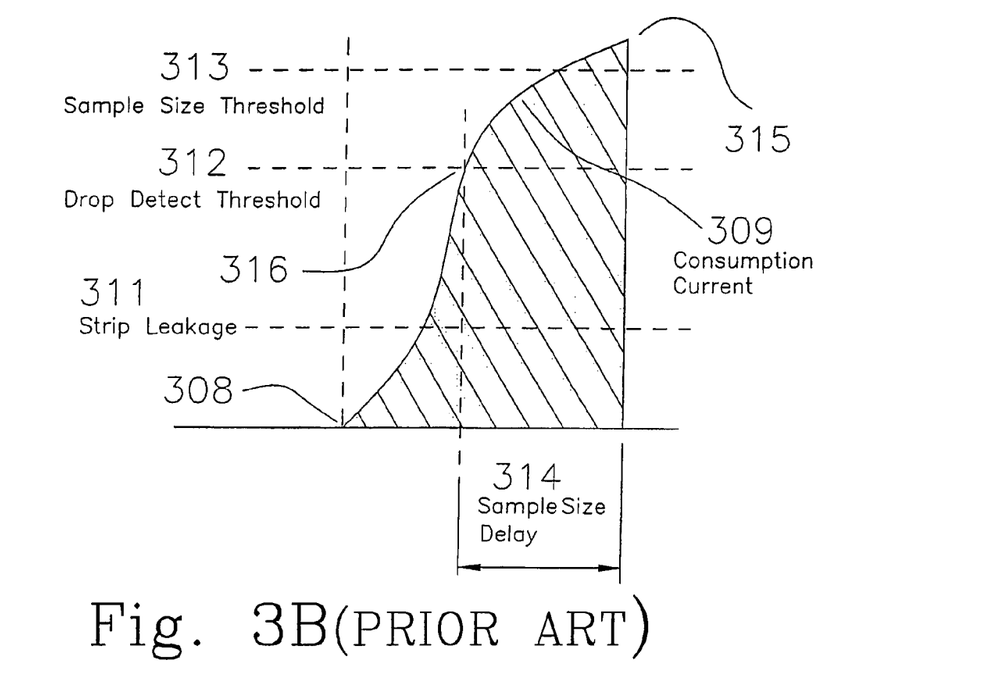
FIGS. 3B-3C are expanded views of current consumed during sample detection in the conventional measuring meters as shown in FIG. 3A.
Figure 3C:
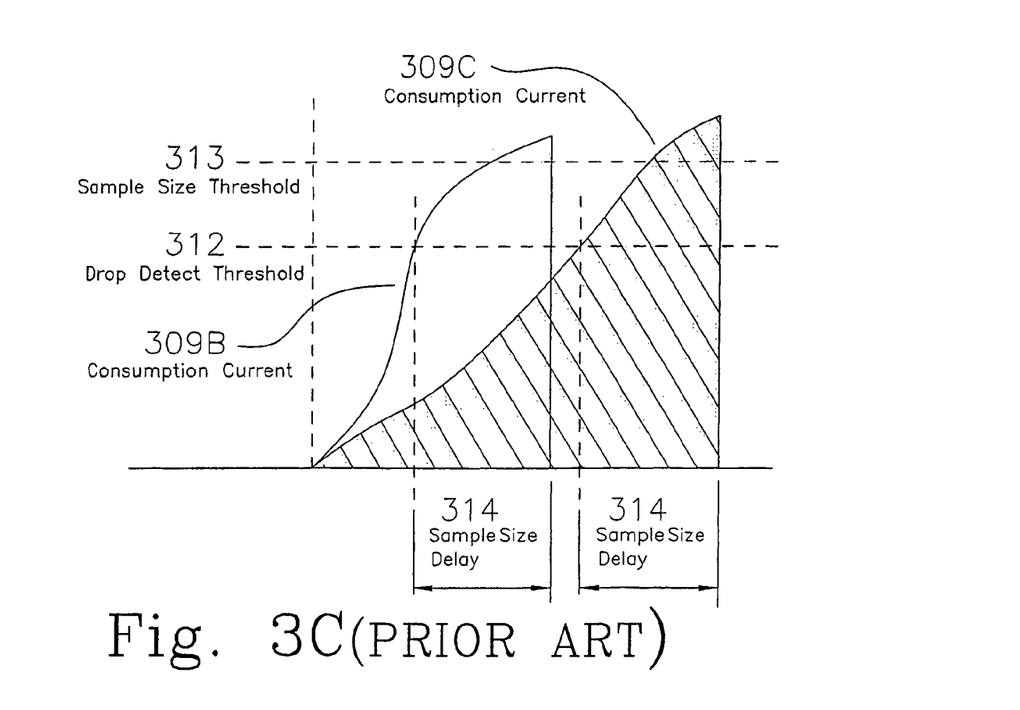

In FIG. 3B an enlarged view of the current flowing at the end of the sample detection period is shown. The area below the curve of the current marked as consumption current 309 is equal to the total current flowing until the end of the sample size delay period 314. It equals the number of electrons consumed during this period of time. This consumption current is due to the reaction between the reagent and the analyte in the test sample. In FIG. 3C, two different consumption currents 309B and 309C depending on different flow speeds of the sample drop are shown. Different flow speeds of the sample lead to a varying end of the sample detection and thus to a varying consumption period. The duration of consumption may vary between 0.04 and 0.3 seconds. The sample flow speed may be affected by manufacturers, e.g. the performance of the capillary channel, the hydrophilic properties of the strip, the ambient temperature or also the conditions of the blood of the user. The blood sample will e.g. flow slowly at low ambient temperature, high HCT or high fat content in the blood. The variability of the consumption duration between 0.04 to 0.3 seconds is relatively high as compared to a short total measurement time of 1 second. Many current glucose monitors have a 5 second total detection time which includes an incubation and measuring period. The measuring period in such cases is about 1 second only. Also, variability may be high for small sample sizes, e.g. used in 1 mL, 0.5 mL and 0.3 mL test strips. Because of current consumption in known measuring meters, measuring errors may be relatively high, especially if small volumes of samples or short detection times are used.

Figure 4:
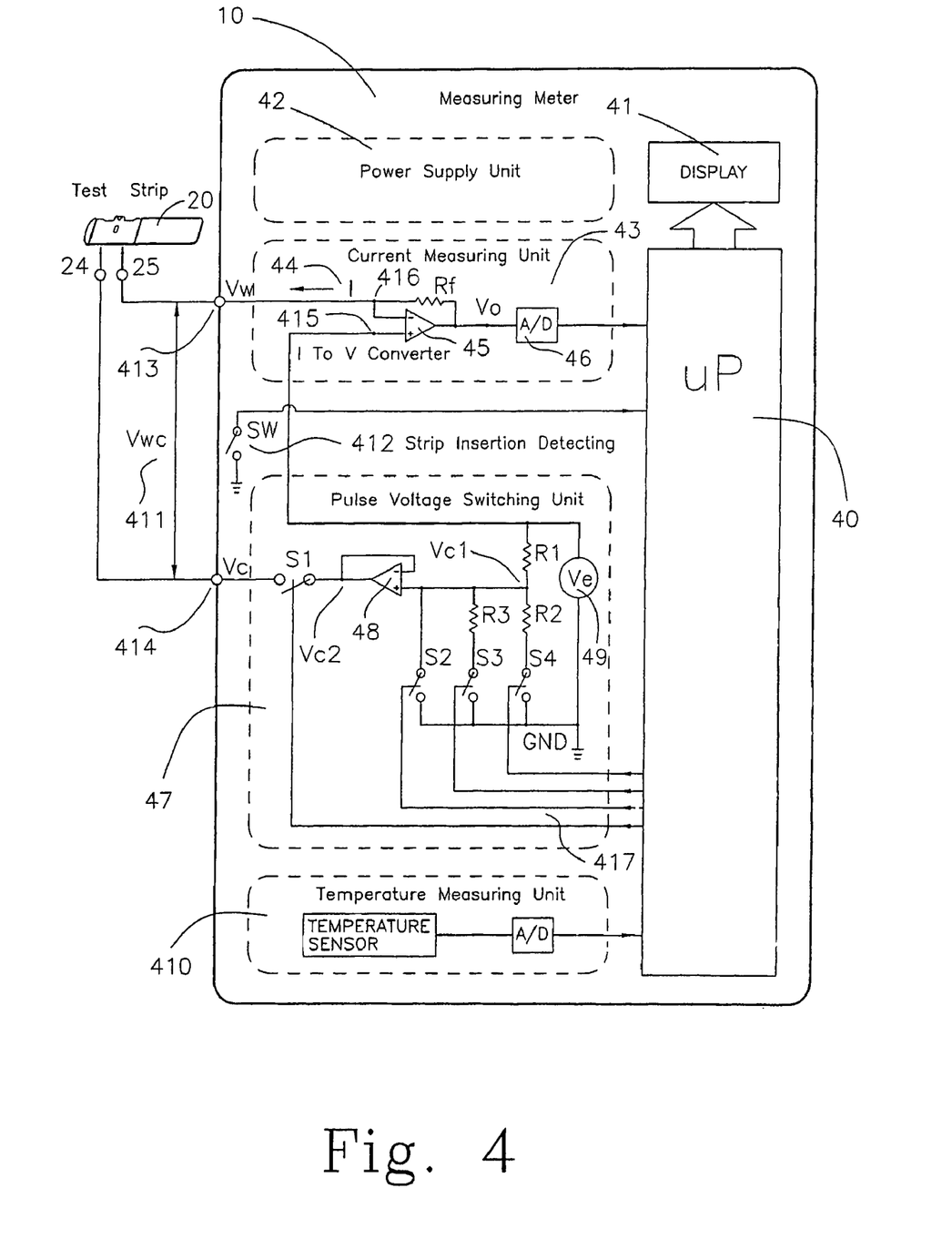
FIG. 4 is a schematic representation of a measuring meter in accordance with the present invention.

FIG. 4 shows a schematic representation of a test meter 10 according to the present invention. The test meter comprises a microprocessor 40, a display 41, a power supply unit 42, a current measuring unit 43, a temperature measuring unit 410, a strip insertion detecting unit 412 with a switch SW and a pulse voltage switching unit 47. Except from the pulse voltage switching unit 47, these parts and the design of the circuit are known to those skilled in the art.

The current measuring unit 43 comprises a current to voltage converter 45 which is used to convert a current 44 flowing between the electrodes 21, 22 (see FIGS. 2A to 2D) to an analogue voltage $V_0$ (where $V_0 = I \times Rf$). The resistance Rf designates the resistance of an electrical conductor through which the current is flowing. An analogue to digital converter 46 converts the analogue voltage $V_0$ to a digital signal which can be input to the microprocessor 40.

The pulse voltage switching unit 47 is used to apply repeatedly varying voltages to the electrodes. The voltage switching unit 47 includes electronic circuits, namely a voltage regulator 49, a voltage divider formed by resistances R1, R2, R3 and switches S2, S3, S4 such as to apply a desired voltage at a point $V_C1$.

A current buffer 48 having a large current driving capacity is used to output a voltage at the point $V_C2$ equal to the voltage at $V_C1$.

A control switch S1 is used to connect and disconnect the point $V_C2$ to the contact 414. Thereby, the voltage of point $V_C2$ can be applied to the point $V_C$.

Furthermore, four control lines 417 are exiting the microprocessor 40 such as to control the switches S1, S2, S3, S4, in particular such as to turn the switches on or off.

The amplitude and duration of the voltage $V_C$ at the point 414 can be controlled by switching the switches S1, S2, S3, S4 in a controlled time sequence of turning off/turning on by the microprocessor 40.

The voltage $V_C$ at the point 414 is:

$$V_C = Ve \times R/(R1+R)$$

Where
R=0 when S2 is switched on, irrespective of the status of switches S3 and S4
R=∞ when all switches S2, S3 and S4 are open
R=R3 when the switch S3 is closed and the other switches are open and
R=R2 when the switch S4 is closed and the other switches are open.

The regulating voltage Ve is applied at point 49 between the ground and contact of the resistance R1. The regulating voltage Ve is further connected to the positive input terminal 415 of the current to voltage converter 45. The voltage of the negative terminal 416 of the current to voltage converter 45 is adjusted to the same voltage level as the positive input terminal 415 automatically by means of an operational amplifier. Consequently, the output voltage at the point $V_W$ is equal to the voltage Ve.

An electrode working voltage $V_{WC}$ 411 (equal to the difference between $V_W$ and $V_C$) is thus applied between contacts 413, 414 such that it can be electrically connected to the contacts 24, 25 of the test strip 20.

Figure 5A:
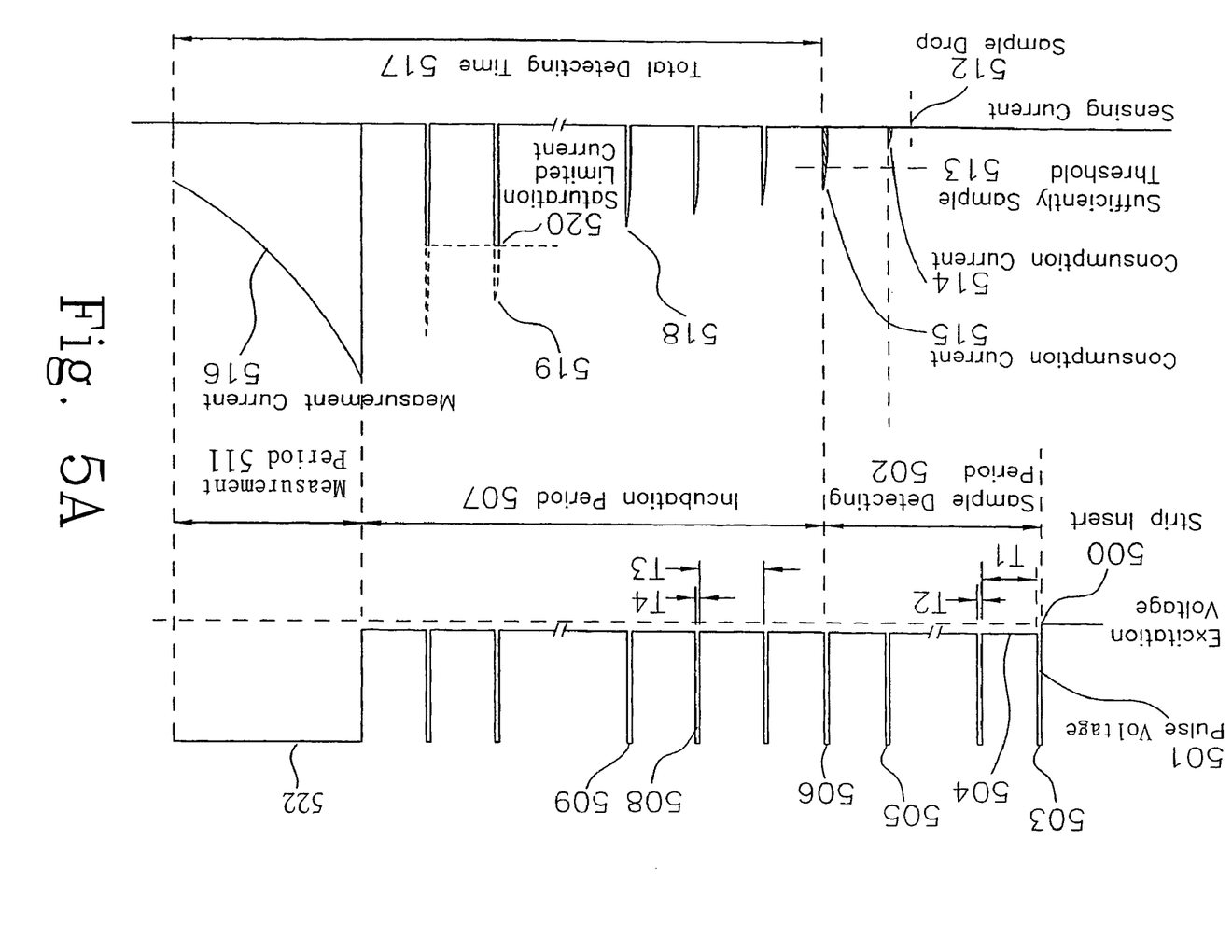
FIG. 5A is a schematic representation of the voltage applied during sample detection and incubation in accordance with a first embodiment of the invention.

FIG. 5A shows a first embodiment of a measuring method according to the present invention. Mechanical insertion of a test strip is detected at a point 500 in traditional manner. When a strip has been inserted, the measuring meter applies a repeated pulsed voltage 501 to the electrodes. This repeated pulsed voltage 501 is used to detect the presence of a sample during the sample detection period 502.

During a subsequent incubation period 507, the same repeatedly varying pulsed voltage 506 is applied to the electrodes.

In a third measurement period 511, a fixed voltage 522 is applied to the electrodes for measuring the Cottrell Current 516. Detection including incubation and measurement lasts for a total detecting time 517. Determination and display of measurement results will be made in a conventional manner thereafter.

Strip insertion is detected by the strip insertion detection unit 412 (see FIG. 4). During the sample detection period 502, the repeatedly pulsed voltage 501 is switched between predetermined high voltage levels 503 and low voltage levels 504. The predefined voltages at the low or high level are controlled by the voltage divider formed by the resistances R1, R2, R3 and the switches S2, S3 and S4 as described hereinabove with respect to FIG. 4.

During the sample detection period 502, a pulsed voltage 501 including a plurality of voltage pulses is applied to the electrodes. These voltage pulses include a repeated increase and decrease of the applied voltage. At the beginning of a pulse, the voltage applied to the electrodes is rapidly increased to a maximum value. At the end of the pulse, the voltage is quickly decreased at a zero or low value. A time difference T1 separates two subsequent pulses. The duration of each of the pulses is equal to T2.

Between subsequent pulses, i.e. during the duration T1, the voltage applied to the electrodes is at a level 504 equal or near to zero. In order to have a zero voltage, the switch S1 (see FIG. 4) is opened. In order to have a low voltage, the switch S1 may be closed. The purpose of having a pulsed voltage during the sample detection period 502 is to reduce the consumption of current during the sample detection period 502. Only during the active duration T2, the switch S1 is turned on and the predefined voltage 503 is applied to the electrodes.

Figure 5B:
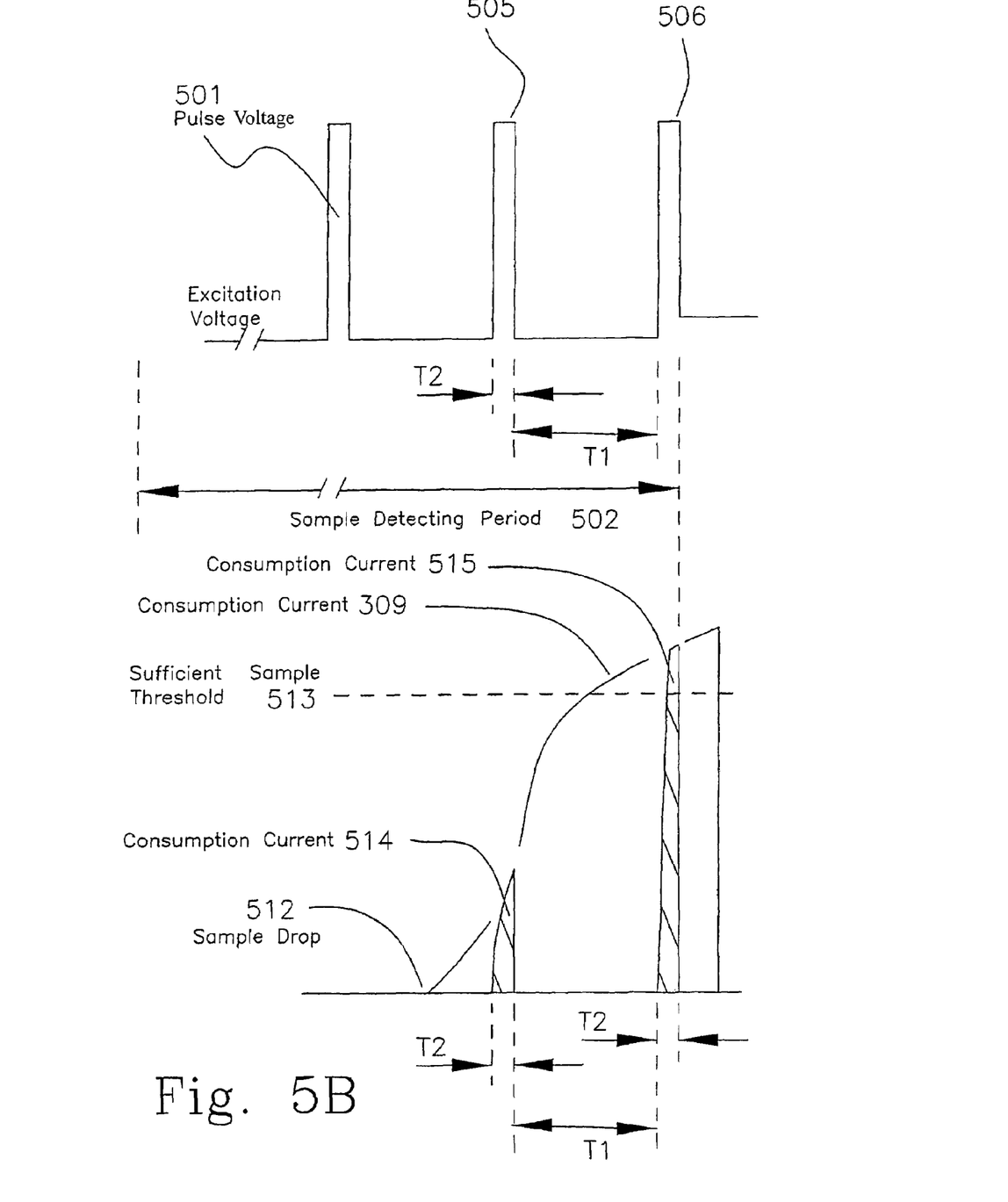
FIG. 5B is an expanded view of the applied voltage during sample detection and the associated consumed current as shown in FIG. 5A.

The current flowing between the electrodes is shown in the lower part of FIG. 5A. FIG. 5B shows an enlarged view of the current flowing during the sample detection period.

The consumption current 309 of prior art methods as shown in FIG. 3B produced by application of a fixed voltage 302 is indicated in FIG. 5B. Because of the application of a pulsed voltage in accordance with the present invention, the consumption current will be only formed by the area 514, 515 below the current curve during the active durations T2.

At the moment 512, a sample drop is applied. The sample is flowing into the test strip in accordance with the description of FIGS. 2C and 2D. Initially, at the moment 512, there is no current flowing between the electrodes because during the inactive period T1 no voltage is applied to the electrodes or only a very low voltage is applied. During the active durations T2, e.g. during the pulse 505 shown in FIG. 5B, a current 514 is flowing between the electrodes once a sample is present. The amplitude of the current is initially less than the sample threshold 513. Consequently, it is considered that not a sufficient amount of sample is present. The meter therefore continues to apply pulsed voltages. In a first, subsequent inactive period T1, no voltage is applied and the flowing current is reduced to zero after the end of the active pulse 505. After the inactive period T1, a new pulse 506 is applied. The amplitude of the current now is above the sample threshold 513 indicating that sufficient sample is present. The meter now stops application of further pulsed voltages and starts the incubation period 507 (see FIG. 5A).

As has been shown with reference to FIG. 5B, the total of consumed current is equal to the sum of the areas below the curve 514 and the curve 515. The amount of consumed current (or consumed electrons) is thus highly reduced as compared to the consumption current in the conventional methods (which is equal to the surface below the curve 309). The optimal selection of the pulse length and cycling time may be determined by experiments. In particular, the time of a pulse, i.e. the active duration T2 may be between 10 μsec. and 300 μsec. The inactive period T1, i.e. the time delay between subsequent pulses may be between 10 msec. and 50 msec. In particular, an active duration T2 of 100 μsec and a inactive time T1 of 20 msec has been turned out to be a good combination.

The time of the pulses, i.e. the active duration T2 is also dependent on the response time of the analogue digital converter 46 (see FIG. 4). Typically, an active time T2 of 100 μsec. is convenient for conventional A/D converter. The selection of the inactive period T1 is made as a compromise between a quick response time for sample presence and low consumption of current.

In accordance with the present invention, the response time of sample presence detection may be twice as fast as the conventional methods shown in FIG. 3B (according to which the sample size detection delay time 314 forming only part of the total detection time is 40 msec).

If for the duration T1 of the inactive status a time of 20 msec. is selected, the duty ratio of the applied voltage and consequently the percentage of consumed current will be as follows:

$$\text{Duty ratio \%}=[T2/(T1+T2)]\times 100\%=[100\ \mu\text{sec.}/(20\ \text{msec.}+100\ \mu\text{sec.})]\times 100\%=0.497\%$$

As compared to the conventional methods (shown in FIG. 3B), the consumption of current during the sample detection period can be reduced by 99.5%.

As mentioned above, the consumption current according to prior art methods (shown in FIG. 3C) is unstable because of different flow speeds of different test samples. With the present invention, the effect of unstable consumption current can be highly reduced. The application of a pulsed voltage during the sample detection period in accordance with the present invention improves precision and accuracy of a measurement, in particular when small test samples are used or when small detection times are used.

In order to solve the problem of oxygen bubbles explained hereinabove, during the incubation period 507 the repeatedly pulsed voltage 508 is applied continuously. In accordance with prior art devices or methods (see FIG. 3A) the fixed voltage 302 is interrupted to a low or zero voltage 304 during the whole incubation period 305 (see FIG. 3A). As explained hereinabove, during this voltage of status 304, oxygen bubbles are produced, which attach to the surface of the electrodes. According to the present invention, a repeatedly pulsed voltage 508 is applied in order to periodically allow the reaction of equation (6). By application of a predefined voltage, the mediator in the reduced form $M_{(RED)}$ can be oxidised to the oxidised form $M_{(OX)}$ of the mediator. This oxidised form $M_{(OX)}$ will compete with the oxygen by reacting with the reduced form of the glucose oxidase (GOD) in accordance with equation (2) and equation (5). By selecting suitable combinations of the amplitude 509 of the pulses 508 during the incubation period 507 and by selecting a suitable duty ratio, enough mediator may be regenerated. Consequently, production of oxygen bubbles will be reduced if the duration T4 of one pulse and the period T3 between subsequent pulses will be appropriately selected as will be shown herein below. During each pulse a current of an amplitude

518, 519 is produced, which may be limited by a saturation current 520, as will be explained with reference to FIG. 7.

The amplitude 509 of the voltage pulses 508 must be selected high enough such as to allow oxidation of the mediator in accordance with equation (6). This voltage 509 should be, however, not high enough in order to allow $H_2O_2$ to oxidise to oxygen, $2H^+$ and electrons in accordance with equation (3) under normal conditions. Usually, about 600 mV of electrode working voltage would be used to oxidise $H_2O_2$. The reaction according to equation (3) will stop almost completely if the predefined voltage 509 is kept below 250 mV. Consequently, the amplitude 509 is typically around 200 mV.

A relatively high duty ratio ensures that enough mediator is regenerated during the incubation period. However, a too high duty ratio will consume a too high amount of current during the incubation period and thus will reduce the measuring current during the measuring period 511. An optimum duty ratio can be determined by way of experiment. Typically, an inactive period T3 of about 10 msec. to 300 msec. and a pulse duration T4 of about 10 μsec. to 1 msec. have shown to be appropriate. The duty ratio in this case typically is between 0.01 and 1%. In practise, the duty ratio may be selected dependent on the type of mediator, the level of the predefined voltage and also of the structure of the electrodes of the test strip. In particular, the pulse duration T4 of 100 μs and the inactive period T3 of 200 ms was found to be appropriate for conventional reagents.

Figure 6A:
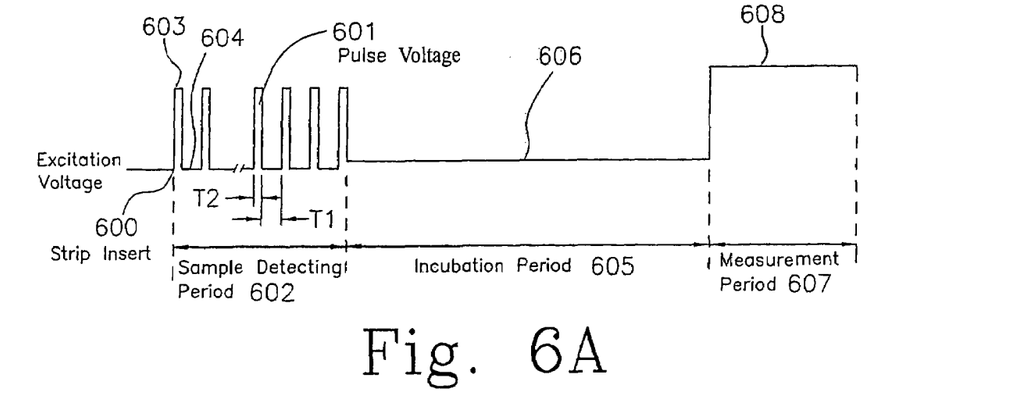
FIGS. 6A-6C are schematic representations of the voltage during sample detection and incubation of three further embodiments of the present invention.
Figure 6B:
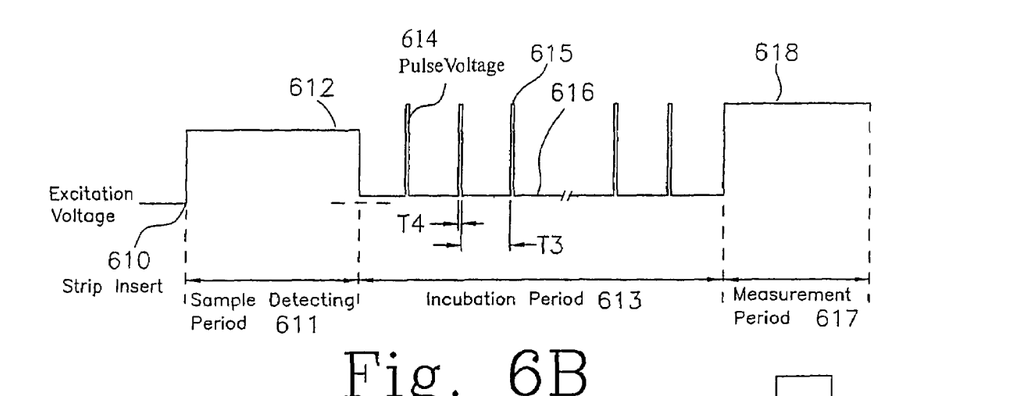
Figure 6C:
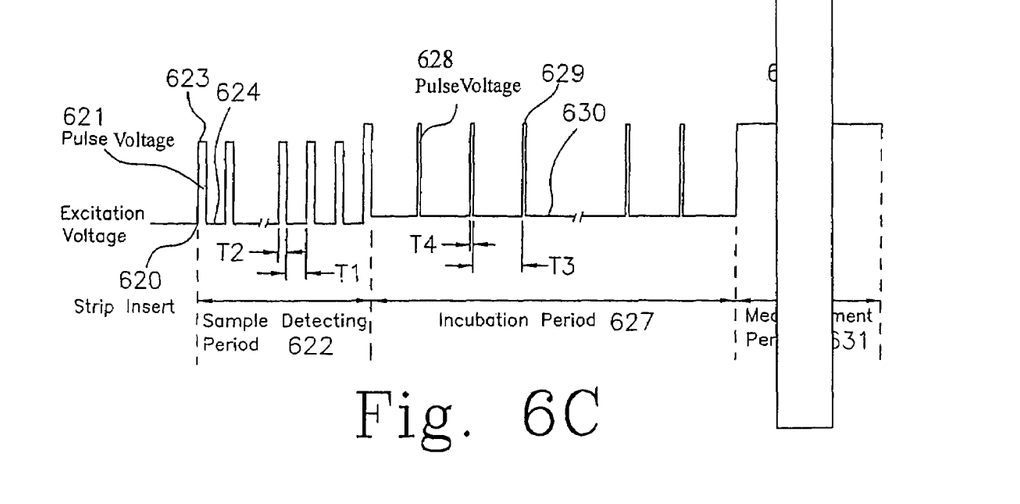

FIGS. 6A to 6C show three further embodiments in accordance with the present invention.

According to FIG. 6A, a repeatedly pulsed voltage 601 varying between a high level 603 and a low level 604 is applied during the sample detection period 602 after strip insertion 600. The pulses applied during this period are substantially identical to the pulses applied in the sample detection period 502 shown with reference to FIG. 5A. Consumption of current is reduced. However, unlike in FIG. 5A, during the incubation period 605 a constantly low voltage 606 is applied. In accordance with the embodiment in FIG. 6A, consumption of current during sample detection period 602 will be reduced. During a measurement period 607 a higher voltage 608 is applied.

FIG. 6B shows a further alternative embodiment. Unlike FIG. 5A, a fixed voltage 612 is applied after strip insertion at point 610 during the sample detection period 611. A repeatedly pulsed voltage 614 varying between a high level 615 and a low level 616 is applied during the incubation period 613 in a manner similar to the repeatedly pulsed voltage applied in the method explained with reference to FIG. 5A. Therewith, generation of oxygen gas bubbles can be reduced. Measurement is made by applying a voltage 618 during a measurement period 617.

FIG. 6C shows a third embodiment of the invention. During a sample detection period 622 after strip insertion at 620, a repeatedly pulsed voltage 621 varying between a high voltage state 623 and a low voltage state 624 is applied in a manner similar to the one explained with reference to FIG. 5A. During the incubation period 627, a repeatedly pulsed voltage 628 varying between a high state 629 and a low state 630 is applied. Unlike FIG. 5A, the pulse times T2, T4 during the sample detection period 622 and the incubation period 627 are different from each other. Also, the inactive time T1, T3 and the high state 623, 629 and the voltage levels at the low states 624, 630 are different in the sample detection period 622 and in the incubation period 627. By specifically selecting these parameters, an optimum result in view of current consumption and generation of oxygen bubbles can be achieved. Measurement during a measurement period 631 is made by application of a voltage 632.

Figure 7:
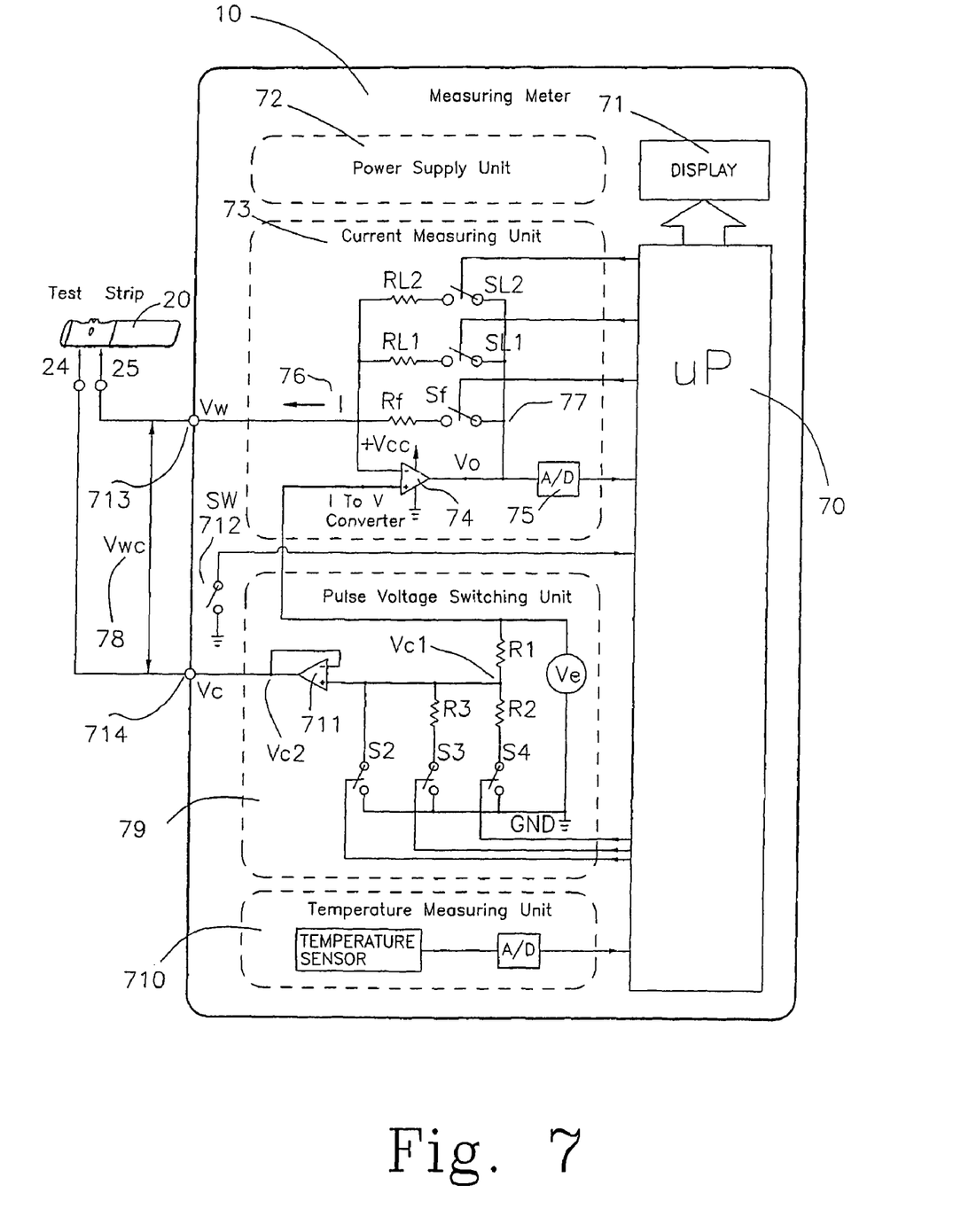
FIG. 7 is a schematic representation of an alternative embodiment of a measuring meter in accordance with the present invention.

FIG. 7 shows an alternative embodiment of a measuring meter in accordance to the invention. Basically, the measuring meter 10 has the same units as the one shown in FIG. 4, in particular a microprocessor 70, a display 71, a power supply unit 72, a current measuring unit 73, a temperature measuring unit 710, a strip insertion detecting unit 712 with a switch SW and a pulse voltage switching unit 79. As compared to FIG. 4, in accordance with FIG. 7, the control switch S1 has been removed between the points $V_C2$ and $V_C$. All other switches S2, S3, S4 are still present.

Switches SL1, SL2 and Sf are arranged in the current measuring unit 73. A current buffer 711 is directly connected to point 714.

The pulse voltage switching unit 79 is used to switch the amplitude of the predefined voltage at the contact point $V_C$ only. To output the desired predefined voltage $V_C$ at the point 714, switches S2, S3 and S4 are controlled by the microprocessor 70.

The current measuring unit 73 comprises a current to voltage converter 74 which is used to convert a current I in a branch 76 flowing between the electrodes 21, 22 (see FIGS. 2A to 2D) to an analogue voltage Vo at a point 77. An analogue to digital converter 75 converts the analogue voltage Vo at point 77 to a digital signal which will be input into the microprocessor 70.

The current to voltage converter 45 in accordance with FIG. 4 is formed by a feedback resistor Rf and an operational amplifier 45.

Contrary to this, in accordance with FIG. 7, a circuit with three branches connected in parallel is used to provide a feedback connection with the operational amplifier.

In a first branch of the circuit, a feedback resistor Rf is connected in series with a switch Sf. In a secondary branch, a resistor RL1 is connected in series with a switch SL1. In a third branch, a resistor RL2 is connected in series with a switch SL2. The switches SF, SL1 and SL2 are controlled and turned in their on/off state by the microprocessor 70. Thereby, either one of the resistances Rf, RL1 or RL2 may be used for feedback connection with the operational amplifier 74.

During the sample detection period and the measurement period, the resistance Rf is activated by closing the switch SF, and the other switches are turned off. The output voltage Vo of the current to voltage converter 74 thus equals to $$Vo = I \times Rf$$

which is the same as the output voltage Vo in accordance with FIG. 4.

During the measurement, a working voltage $V_{WC}$ 78 is applied between the points 714 (having the voltage $V_C$) and 713 (having a working voltage $V_W$) provided.

The resistors RL1 and RL2 are used during incubation period 507 (see FIG. 5A) in order to limit the amplitude 518, 519 of the current generated during incubation period 507 (see FIG. 5A).

During the measurement period 511, the output voltage Vo is (see above) proportionally increasing with the measuring current I in the branch 76. However, the output value Vo cannot increase to any value. When the output voltage Vo has reached a maximum saturation voltage of the operational amplifier of the current to voltage converter 74, it will stop to further increase. Usually, for normal amplifiers, the saturation voltage is about 1.2 to 1.8 volt below the value of the positive supply voltage Vcc. If e.g. the positive supply voltage of the operational amplifier Vcc is 5 volt, the saturation voltage will be around 3.8 volt.

Because of this limitation, selection of an optimum resistance for the feedback Rf for desired current measuring range will be necessary.

Typically, a resistance Rf of 27 KΩ is suitable for a current in the range between 0 and 100 μA in a system having a supply voltage Vcc of 5 volt.

For such parameters, the maximum saturation current Isat will be $$Isat=(Vsat-Vc)/Rf$$

where Vc is the voltage at the point 714 shown in FIG. 7. For such a system, the saturation current is about 120 μA.

During the incubation period 507 shown in FIG. 5A, a repeatedly pulsed voltage 508 is applied to the electrodes in order to minimise the effect of oxygen bubbles. After a certain incubation time, the test sample is completely mixed and melted with the reagent. Consequently, a large pulse current will be produced at each active duration 509. Especially with samples having a high concentration of analytes, the pulse current will be limited by the maximum of the saturation current $I_{SAT}$ explained hereinabove. After completing incubation, a saturation current 520 (see FIG. 5A) of 120 μA flows between the electrodes during each active duration 509 if a 27 KΩ resistance is used for Rf. It is not necessary to have higher currents in order to minimise the effect of oxygen gas bubble production.

According to this embodiment of the invention, the use of limited resistors RL1 or RL2 having 120 KΩ and 680 KΩ respectively is proposed. These different resistances can be applied for different concentrations of analytes in the testing samples.

The voltage Vo can be measured by the microprocessor. In answer to a measurement result, either switch SL1 or switch SL2 can be turned on.

As has been shown in FIG. 5A, the pulse current amplitude 519 will be increased if a resistance Rf of 27 KΩ is used. The pulse current is limited to a saturation limited pulse current 520 (see FIG. 5A) if the resistance RL1 (120 KΩ) is used as a feedback resistor, and the saturation current will be about 27 μA. Thus it will reduce current consumption during the incubation time.

It is also possible to turn all switches SF, SL1 and SL2 simultaneously off such as to completely interrupt the applied voltage.

It is to be understood that the invention need not be limited to the disclosed embodiment. On the contrary, it is intended to cover various modifications and similar arrangements included within the spirit and scope of the appended claims, which are to be accorded with the broadest interpretation so as to encompass all such modifications and similar structures.

What is claimed is:

1. A method for operating a measuring meter for an electrochemical test strip, comprising steps of:
   providing a series of pulse voltages to electrodes of the test strip during both a sample presence detection period and an incubation period, wherein a duration of pulses during the sample presence detection period is from 10 μs to 300 μs, a duration between successive pulses is from 10 ms to 50 ms, a maximum value of the series of pulse voltages provided during the incubation period is sufficiently high to oxidize a reduced form of a mediator $M_{(RED)}$ in a reagent of the test strip into its oxidised form $M_{(OX)}$, and sufficiently low so as to avoid an oxidation of an $H_2O_2$ in the reagent; and
   providing a fixed voltage to electrodes of the test strip during a measurement period.

2. A method according to claim 1, wherein the voltage is provided in a regular pattern with one of a predetermined and a predeterminable frequencies and with a maximum value which is constant during at least one of the periods.

3. A method according to claim 1, wherein a minimum value of the series of pulse voltages between two successive pulses is 0 Volt.

4. A method according to claim 1, wherein a minimum value of the pulse voltage between two successive pulses is larger than 0 Volt, but less than 0.1 Volt.

5. A method according to claim 1, wherein a duration between two successive pulses is operated by an open circuit.

6. A method according to claim 1, wherein a duration of pulses during the sample presence detection period is 100 μs, and a duration between successive pulses is 20 ms.

7. A method according to claim 1, wherein a duration of pulses during the incubation period is from 10 μs to 1 ms, and a duration between successive pulses is from 10 ms to 300 ms.

8. A method according to claim 1, wherein a duration of pulses during the incubation period is 100 μs, and a duration between successive pulses is 200 ms.

9. A method according to claim 1, wherein a maximum value of the series of pulse voltages provided during the sample presence detection period is sufficient for creating a measurable current between the electrodes when a sample is present.

10. A method according to claim 1, further comprising a step of limiting a flowing current between the electrodes during the incubation period.

11. A method according to claim 1, wherein a maximum value of the series of pulse voltages between two successive pulses is larger than 0.1 Volt, but less than 0.6 Volt.

12. A method for operating a measuring meter for an electrochemical test strip, comprising steps of:
   providing a series of pulse voltages to electrodes of the test strip during a sample presence detection period, wherein a duration of pulses during the sample presence detection period is from 10 μs to 300 μs, a duration between successive pulses is from 10 ms to 50 ms; and
   providing a first fixed voltage to the electrodes of the test strip during an incubation period, wherein the first fixed voltage provided during the incubation period is in a range between being sufficiently high to oxidize a reduced form of a mediator $M_{(RED)}$ in a reagent of the test strip into its oxidised form $M_{(OX)}$ and being sufficiently low so as to avoid an oxidation of an $H_2O_2$ in the reagent.

13. A method according to claim 12, further comprising a step of providing a second fixed voltage to the electrodes of the test strip during a measurement period, wherein the first fixed voltage is lower than the second fixed voltage.

14. A measuring meter for an electrochemical test strip, comprising:
   a voltage providing device programmed to provide a series of pulse voltages to electrodes of the test strip during both a sample presence detection period and an incubation period, and provide a fixed voltage to electrodes of the test strip during a measurement period, wherein a duration of pulses during the sample presence detection period is provided from 10 μs to 300 μs, a duration between successive pulses is provided from 10 ms to 50 ms, the series of pulse voltages provided by the voltage providing device during the incubation period have a maximum value being sufficiently high to oxidize a reduced form of a mediator $M_{(RED)}$ in a reagent of the test strip into its oxidised form $M_{(OX)}$, and sufficiently low so as to avoid an oxidation of an $H_2O_2$ in the reagent; and a limiting device limiting a current flow between the electrodes during the incubation period, wherein the limiting device is formed by at least two resistors which are selectively connected to an entry of an operational amplifier of a current to voltage converter, and each of the resistors is connected with a switch in series to switch on/off the resistors respectively.

15. A measuring meter according to claim 14, wherein the voltage providing device provides the voltage in a regular pattern with one of a predetermined and a predeterminable frequencies.

16. A measuring meter according to claim 14, wherein the pulse voltage providing device provides the voltage being 0 Volt between two successive pulses.

17. A measuring meter according to claim 14, wherein the pulse voltage providing device provides the voltage being larger than 0 Volt but less than 0.1 Volt between two successive pulses.

18. A measuring meter according to claim 14, wherein the pulse voltage providing device provides the voltage consisting of pulses with a duration thereof being 100 µs, and a duration between the successive pulses is 20 ms during the sample presence detection period.

19. A measuring meter according to claim 14, wherein the pulse voltage providing device provides the voltage consisting of pulses with a duration thereof being 10 µs to 1 ms, and a duration between the successive pulses is 10 ms to 300 ms during the incubation period.

20. A measuring meter according to claim 14, wherein the pulse voltage providing device provides the voltage consisting of pulses with a duration thereof being 100 µs, and a duration between the successive pulses is 200 ms during the incubation period.

21. A measuring meter according to claim 14, wherein the series of pulse voltages provided by the voltage providing device during the sample presence detection period are sufficient for creating a measurable current between the electrodes when a sample is present.

* * * * *